(12) United States Patent
Sauers et al.

(10) Patent No.: US 8,658,108 B2
(45) Date of Patent: Feb. 25, 2014

(54) LIMITED-USE BLOOD GLUCOSE METERS

(75) Inventors: Matthew C. Sauers, Indianapolis, IN (US); Robert G. Davies, Carmel, IN (US); Colleen Csavas, Bukit Tunku (MY); Carol J. Batman, Indianapolis, IN (US); Paul S. Rutkowski, Carmel, IN (US); Randy J. Gardner, Bloomington, IN (US); Michael J. Blackburn, Indianapolis, IN (US); Michel A. Cadio, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 166 days.

(21) Appl. No.: 12/873,697

(22) Filed: Sep. 1, 2010

(65) Prior Publication Data
US 2012/0053436 A1  Mar. 1, 2012

(51) Int. Cl.
*G01N 33/00* (2006.01)
(52) U.S. Cl.
USPC ............................ 422/404; 422/500; 422/68.1
(58) Field of Classification Search
USPC ......................................... 422/404, 500, 68.1
See application file for complete search history.

(56) References Cited

U.S. PATENT DOCUMENTS

| | | |
|---|---|---|
| 5,580,794 A | 12/1996 | Allen |
| 5,837,546 A | 11/1998 | Allen et al. |
| 5,961,451 A | 10/1999 | Reber et al. |
| 7,804,483 B2 * | 9/2010 | Zhou et al. ................... 345/107 |
| 2001/0043205 A1 | 11/2001 | Huang et al. |
| 2002/0002326 A1 | 1/2002 | Causey, III et al. |
| 2006/0275890 A1 | 12/2006 | Neel et al. |
| 2007/0158189 A1 | 7/2007 | Yang et al. |
| 2008/0299009 A1 | 12/2008 | Angelides |
| 2009/0051560 A1 | 2/2009 | Manning et al. |

FOREIGN PATENT DOCUMENTS

WO    2009/143943 A1    12/2009

* cited by examiner

*Primary Examiner* — Sam P Siefke
(74) *Attorney, Agent, or Firm* — Dinsmore & Shohl LLP

(57) ABSTRACT

A limited-use blood glucose meter includes a printed circuit board assembly that includes a power source, a strip port, a strip reading device, a controller device, a bi-stable display, and a display controller. The strip reading measures a reaction between a blood sample present on the blood glucose test strip and the blood glucose reagent, generates a blood glucose signal, and calculates a blood glucose level. The controller device receives the blood glucose level from the strip reading device. The controller device provides display instructions to the display controller and the display controller provides drive voltages to the bi-stable segments such that the bi-stable segments persistently display the most-recent blood glucose level. The strip reading device performs a predetermined number of blood glucose tests and calculates a blood glucose level only for blood glucose strips associated with the disposable blood glucose meter.

19 Claims, 6 Drawing Sheets

LIMITED-USE BLOOD GLUCOSE METERS

TECHNICAL FIELD

The present specification relates generally to blood glucose meters and, more particularly, limited-use blood glucose meters incorporating bi-stable displays.

BACKGROUND

As background, persons with diabetes suffer from either Type I or Type II diabetes in which the glucose level in the blood is not properly regulated by the body. As a consequence, many persons with diabetes often carry specialized electronic monitors, called blood glucose (bG) monitors, to periodically measure their glucose level and take appropriate action, such as administering insulin. Blood glucose monitors commonly comprise a base unit that houses control and test electronics required to test the glucose level in a sample of blood. Typical bG monitors may also have a measurement strip receptacle that accepts a disposable measurement strip. One end of the strip is inserted into the measurement strip receptacle while an exposed area contains a reaction site in which the user deposits a drop of blood, which is often obtained by pricking the skin with a lancet. Conductors run from the reaction site, which comprises various reagent chemicals, to the end inserted into base unit, thereby electrically coupling the reaction site to the control and test electronics.

Current bG monitors are expensive devices that have many features, such as a large memory for storing a large amount of bG measurement data, wireless capabilities to communicate with other device such as computers and mobile telephones, graphing capabilities, etc. In many instances a user may not require such an expensive bG monitor. A user may buy many bG monitors to have at various locations, such as in the car, at home, and at work so he or she is never without a monitor. Having so many bG monitors may be expensive for the user. Requiring a user to purchase an expensive bG monitor when he or she forgets it at home or another location is undesirable. Additionally, a user may not wish to take such an expensive (and perhaps bulky) device traveling or during physical activities for fear of loss or damage to the monitor. In another instance, a person who suspects that he may have diabetes most likely does not wish to spend money on expensive devices to determine whether or not he has diabetes. Similarly, a woman with gestational diabetes most likely does not want to purchase an expensive bG monitor for use only during her pregnancy.

Accordingly, a need exists for alternative blood glucose measuring devices that are both inexpensive and effective.

SUMMARY

In one embodiment, a limited-use blood glucose meter includes a printed circuit board assembly. The printed circuit board assembly includes a power source, a strip port, a strip reading device, a controller device, a bi-stable display, and a display controller. The strip port is configured to accept a blood glucose test strip having a blood glucose reagent. The strip reading device is electrically coupled to the strip port which measures a reaction between a blood sample present on the blood glucose test strip and the blood glucose reagent, generates a blood glucose signal corresponding with the measured reaction, and which calculates a blood glucose level based at least in part on the blood glucose signal. The controller device is communicatively coupled to the strip reading device and receives the blood glucose level from the strip reading device. The bi-stable display includes a plurality of bi-stable segments which transition between an on-state and an off-state with the application of drive voltages. The bi-stable segments are arranged to display the blood glucose level, and the bi-stable display persistently displays a most-recent blood glucose level without power provided by the power source. The display controller is communicatively coupled to the controller device and the bi-stable display. The controller device provides display instructions to the display controller and the display controller provides drive voltages to the bi-stable segments based on the blood glucose level such that the bi-stable segments persistently display the most-recent blood glucose level. The strip reading device performs a predetermined number of blood glucose tests and calculates a blood glucose level only for blood glucose test strips associated with the limited-use blood glucose meter.

In another embodiment, a limited-use blood glucose meter includes a printed circuit board assembly. The printed circuit board assembly includes a non-removable battery, a strip port, a strip reading device, a bi-stable display, and a display controller. The strip port accepts a blood glucose test strip having a blood glucose reagent. The strip reading device is electrically coupled to the strip port and measures a reaction between a blood sample present on the blood glucose test strip and the blood glucose reagent, generates a blood glucose signal corresponding with the measured reaction, and calculates a blood glucose level based at least in part on the blood glucose signal. The bi-stable display includes a plurality of bi-stable segments which transition between an on-state and an off-state with the application of drive voltages. The bi-stable segments are arranged to display the blood glucose level. The bi-stable display persistently displays a most-recent blood glucose level without power provided by the non-removable battery until a subsequent blood glucose level is calculated. The display controller is communicatively coupled to the bi-stable display, wherein the display controller receives display instructions and provides drive voltages to the bi-stable segments based on the blood glucose level and the display instructions such that the bi-stable segments persistently display the most-recent blood glucose level. The strip reading device performs a predetermined number of blood glucose tests and calculates a blood glucose level only for blood glucose test strips associated with the limited-use blood glucose meter.

In yet another embodiment, a limited-use blood glucose meter includes a printed circuit board assembly and a meter housing. The printed circuit board assembly consists essentially of a non-removable battery, a strip port, a strip reading device, a controller device, a bi-stable display, a display controller, and a memory device. The meter housing includes a lens and a strip port opening. The strip port accepts a blood glucose test strip having a blood glucose reagent. The strip reading device is electrically coupled to the strip port and measures a reaction between a blood sample present on the blood glucose test strip and the blood glucose reagent, generates a blood glucose signal corresponding with the measured reaction, and calculates a blood glucose level based at least in part on the blood glucose signal. The controller device is communicatively coupled to the strip reading device, wherein the controller device receives the blood glucose level from the strip reading device. The bi-stable display includes a plurality of bi-stable segments which transition between an on-state and an off-state with the application of drive voltages. The bi-stable segments are arranged to display the blood glucose level, and the bi-stable display persistently displays a most-recent blood glucose level without power provided by the non-removable battery. The display controller is communicatively coupled to the controller device and the bi-stable display, and provides drive voltages to the bi-stable segments based on the blood glucose level such that the bi-stable segments persistently display the most-recent blood glucose level. The memory device is communicatively coupled to the strip reading device and the controller device. The memory device stores the most-recent blood glucose level, and the display controller retrieves the most-recent blood glucose level from the memory device upon instruction from the controller device. The meter housing defines an enclosure in which the printed circuit board assembly is disposed such that the bi-stable display is aligned with the lens. The lens is dimensioned such that the bi-stable display is visible through the lens. The strip port opening is aligned with the strip connection port and sized to accept the blood glucose test strip.

These and other advantages and features of the embodiments disclosed herein, will be made more apparent from the description, drawings and claims that follow.

BRIEF DESCRIPTION OF THE DRAWINGS

The following detailed description of the embodiments of the present specification can be best understood when read in conjunction with the following drawings, where like structure is indicated with like reference numerals, and in which.

DETAILED DESCRIPTION

Figure 1A:
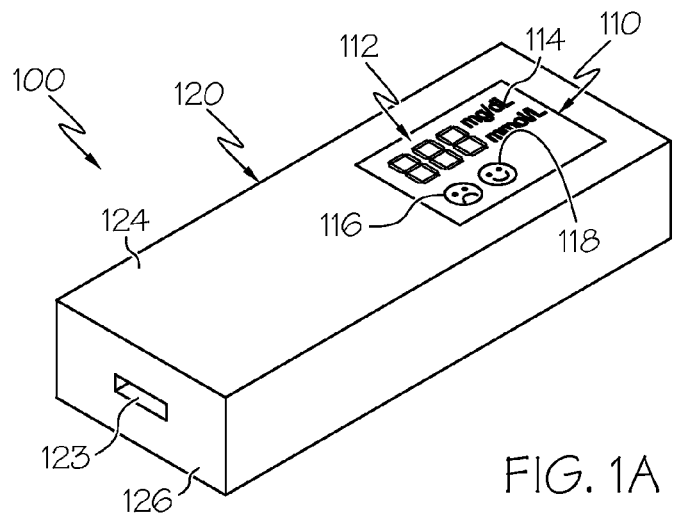
FIG. 1A is a perspective view of a limited-use blood glucose meter according to one or more embodiments described and illustrated herein.

Referring initially to the figures, FIG. 1A in particular, embodiments described herein relate generally to blood glucose meters for the measurement of blood glucose levels. Embodiments may be considered limited-use or disposable blood glucose meters, meaning that they are low-cost devices that are programmed or otherwise configured to only perform a certain number of blood glucose measurement tests. After the completion of the number of tests, the limited-use blood glucose meter may be disposed of. Embodiments utilize a persistent bi-stable display such as e-paper, for example, to both display and store a most-recent blood glucose level. Because the bi-stable display persistently displays the most-recent blood glucose level even when the meter is powered down, the bi-stable display acts as a memory device. Therefore, a common memory device such as flash memory is not required to store all of the previous results. Eliminating a large flash memory device from the circuit reduces the cost of the meter, which enables the meter to be disposable. As described in more detail below, a user may record the most-recent blood glucose level onto or into any type of medium, such as a specialized form (e.g., on a paper form or a computerized form), on a piece of paper, a website, etc. Once the user has performed the predetermined number of blood glucose tests, the limited-use blood glucose meter may cease to operate and the user may dispose of the meter. Embodiments of the limited-use blood glucose meter will be described in more detail herein.

Figure 1B:
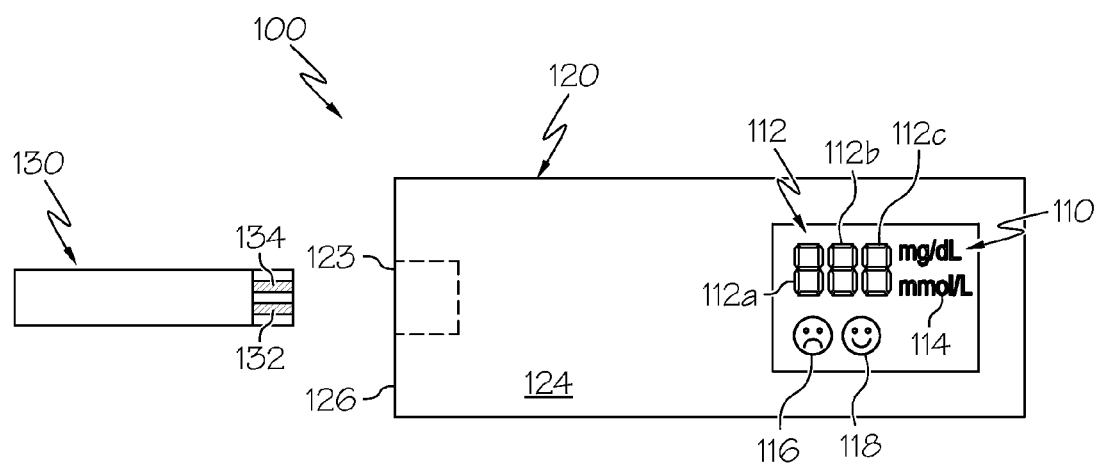
FIG. 1B is a top view of a limited-use blood glucose meter according to one or more embodiments described and illustrated herein.
Figure 1C:
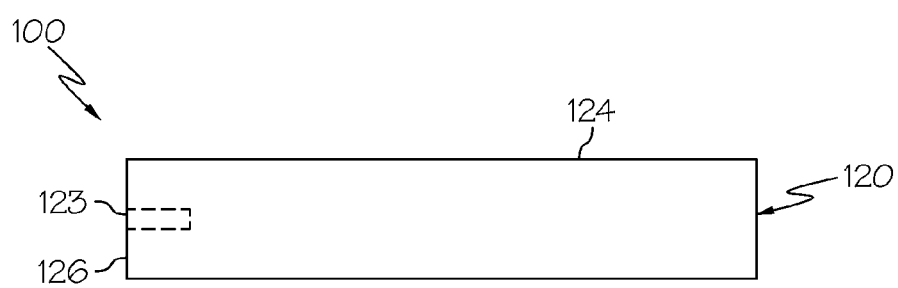
FIG. 1C is a side view of a limited-use blood glucose meter according to one or more embodiments described and illustrated herein.

Referring specifically to FIGS. 1A-1C, one embodiment of a limited-use blood glucose meter 100 is illustrated. The limited-use blood glucose meter 100 generally comprises a meter housing 120, a bi-stable display 110 disposed within the meter housing 120, and a strip port opening 123. The meter housing 120 may comprise any number of shapes and sizes. The embodiment illustrated in FIGS. 1A-1C has a generally rectangular shape. In one embodiment, the meter housing 120 defines a limited-use blood glucose meter 100 that is relatively small in size. For example, the limited-use blood glucose meter 100 may be similar in size to a USB "thumb drive" flash memory device. As an example and not a limitation, the limited-use blood glucose meter 100 may have a length l of approximately 35 mm, a width w of approximately 20 mm, and a height h of approximately 10 mm. It should be understood that embodiments may possess other dimensions. The limited-use blood glucose meter 100 comprises a first side 124 from which the bi-stable display is visible and a front side into which a blood glucose test strip 130 may be inserted.

Figure 2A:
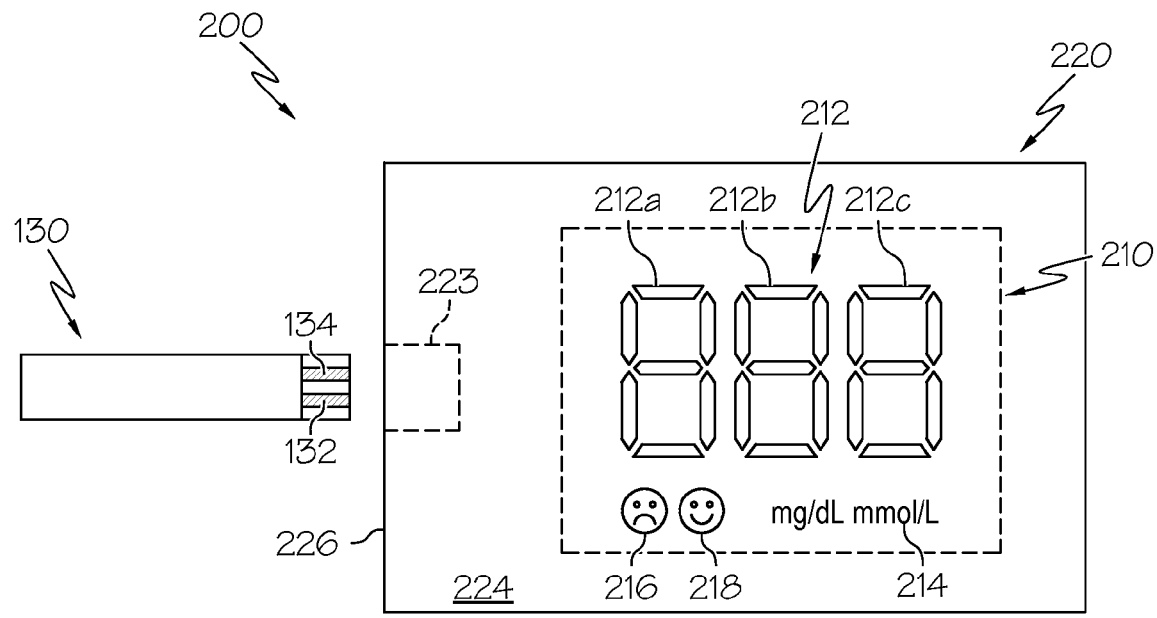
FIG. 2A is a top view of a limited-use blood glucose meter according to one or more embodiments described and illustrated herein.
Figure 2B:
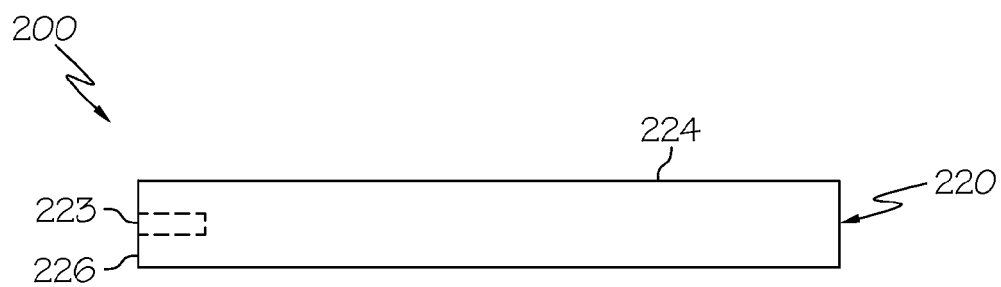
FIG. 2B is a side view of a limited-use blood glucose meter according to one or more embodiments described and illustrated herein.

An exemplary embodiment of a limited-use blood glucose meter 200 having a geometry that is different from the limited-use blood glucose meter 100 illustrated in FIGS. 1A-1C is illustrated in FIGS. 2A and 2B. The elements of the embodiment illustrated in FIGS. 2A and 2B are similar to those illustrated in FIGS. 1A-1C. The limited-use blood glucose meter 200 has a meter housing 220 that has a size and geometry that is similar to that of a credit card such that the limited-use blood glucose meter 200 may be easily carried in a wallet or other pocket-sized carrying case. The meter housing 220 may be thin to enable the limited-use blood glucose meter 200 to be inserted into a sleeve of a wallet. As described above with reference to FIGS. 1A-1C, the limited-use blood glucose meter 200 comprises a bi-stable display 210, which may be larger than the embodiment illustrated in FIGS. 1A-1C, and a strip port opening 223.

Figure 5A:
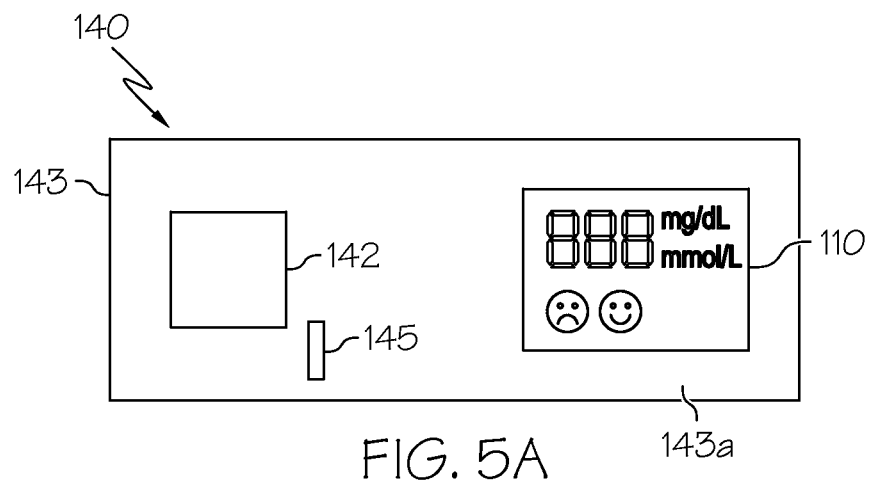
FIG. 5A is a top view of a printed circuit board assembly of a limited-use blood glucose meter according to one or more embodiments described and illustrated herein.
Figure 5B:
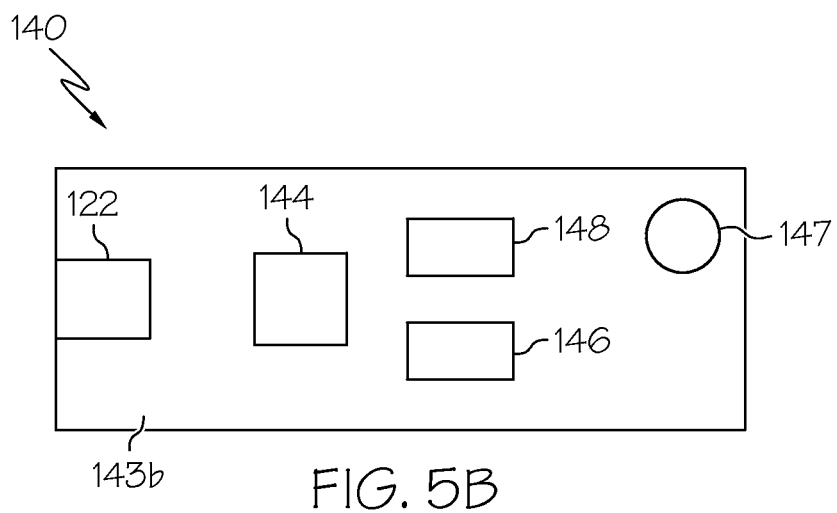
FIG. 5B is a bottom view of a printed circuit board assembly of a limited-use blood glucose meter according to one or more embodiments described and illustrated herein.
Figure 5C:
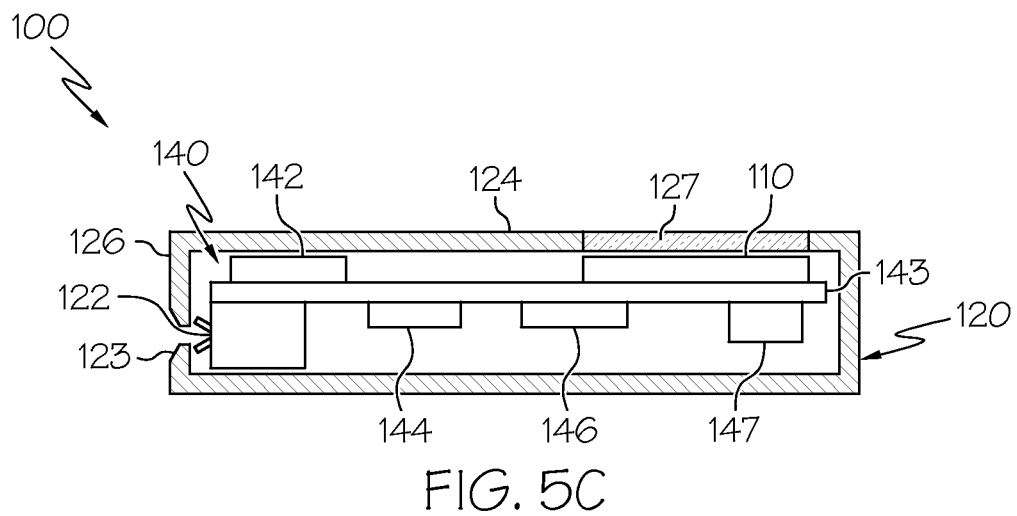
FIG. 5C is a cross section view of a limited-use blood glucose meter according to one or more embodiments described and illustrated herein.

Referring to FIGS. 1A-1C (as well as FIGS. 2A and 2B), the strip port opening 123 is sized and configured to accept a blood glucose test strip 130 (FIG. 1B), which may be removably inserted into the strip port opening 123. As shown in FIG. 5C, the geometry of the strip port opening 123 may provide enough chamfer and guiding surfaces to ease the insertion of the blood glucose test strip 130 into the strip port opening 123. The blood glucose test strip 130 may be configured to receive a blood sample in the form of a blood drop at a reaction site located at a point along the strip, such as near the tip. As described in more detail below, the blood glucose test strip 130 may contain electronic circuitry and/or chemicals (e.g., a reagent) at the reaction site which facilitate the measurement of the blood glucose level of the blood sample through electrodes 132 and 134.

The bi-stable display 110 may be positioned behind a transparent, protective lens 127 of the meter housing 120 (see FIG. 5C). The bi-stable display may be an electrophoretic display, which may display information by rearranging charged particles using an electric field. The bi-stable display persistently displays the most-recent blood glucose level. In other words, the most-recent blood glucose level remains displayed on the bi-stable display 110 until another blood glucose test is performed—even when the limited-use blood glucose meter 100 is in a powered-down state. The bi-stable display 110 is used for electrophoretically displaying a blood glucose level as well as whether or not a particular blood glucose level resulting from a test is good (i.e., falling within a good blood glucose range) or bad (i.e., not falling within the good blood glucose range). The bi-stable display 110 may be of any suitable bi-stable technology or products. As an example and not a limitation, the bi-stable display may be a segmented e-paper display as manufactured by E-Ink Corporation of Cambridge, Mass.

FIGS. 1A and 1B illustrate one embodiment of a bi-stable display. It is noted that the bi-stable display 210 illustrated in FIG. 2A has similar components and configuration and that only the bi-stable display 110 of FIGS. 1A and 1B will be described. The bi-stable display 110 comprises a numeric region 112, units indicator 114, bad blood glucose symbol 116, and good blood glucose symbol 118. In one embodiment, the numeric region 112 includes three seven segment digits 112a, 112b and 112c that are controlled to display a blood glucose level based on a blood glucose measurement test. Each segment of the digits 112a-112c may be turned on and off by the application of charge voltages. In another embodiment, the bi-stable display 110 may be configured as a matrix of controllable pixels that may be driven to display the desired blood glucose measurement or other intended information. The units indicator may include mm/dL and mmol/L unit indicators that may be turned on (i.e., a dark state) depending on the configuration of the limited-use blood glucose meter 100. The bad blood glucose symbol 116 may be in an ON state (and the good blood glucose symbol 118 in an OFF state) when the most-recent blood glucose level is outside of a good blood glucose level range, while the good blood glucose symbol 118 may be in an ON state (and the bad blood glucose symbol 116 in an OFF state) when the most-recent blood glucose level is within the good blood glucose level range. It should be understood that any type of symbol may be used for the good and bad blood glucose symbols and embodiments are not limited to the smile and frown faces illustrated in FIGS. 1A, 1B and 2A.

Each bi-stable segment of the bi-stable display comprises a top electrode and a bottom electrode (not shown). The top electrode is transparent to allow ambient light to pass through. Between the top and bottom electrodes is a layer containing colored oil (e.g., black oil) that suspends white particles having a particular charge. To control the bi-stable segment, a voltage may be applied across the top and bottom electrodes. The charged particles will migrate toward the electrode having the charge that is opposite to the charge of the particles. When the particles are located near the top electrode (e.g., the particles are negatively charged and a positive voltage is or was recently present at the top electrode), the bi-stable segment will appear white or "off" because ambient light reflects off of the particles. Conversely, when the particles are located near the bottom electrode (e.g., the particles are negatively charged and a positive voltage is or was recently present at the bottom electrode), ambient light is absorbed by the colored oil, making the bi-stable segment appear dark or "on." Because the display is bi-stable, the bi-stable segment remains in its present state until a voltage having a reverse polarity is applied to the top and bottom electrodes. It should be understood that other bi-stable display configurations may be utilized, such as bi-stable displays that use black and white ink, or rotating balls having a first color on one side and a second color on the opposite side, for example.

Figure 3A:
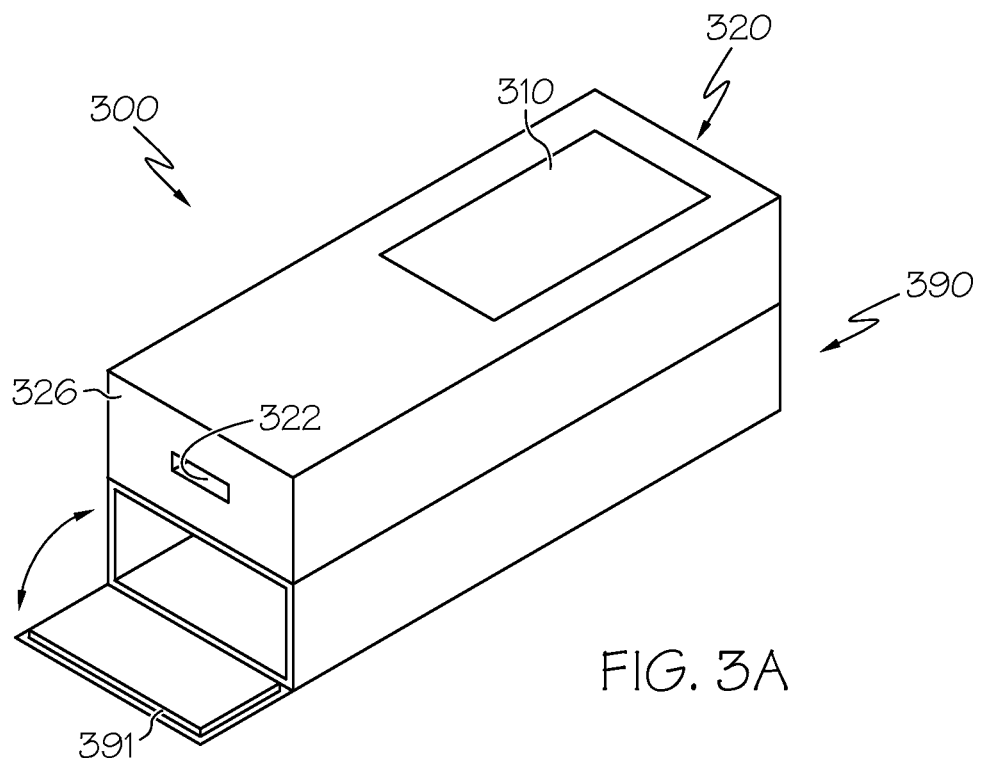
FIG. 3A is a perspective view of a limited-use blood glucose meter having a blood glucose test strip enclosure according to one or more embodiments described and illustrated herein.
Figure 3B:
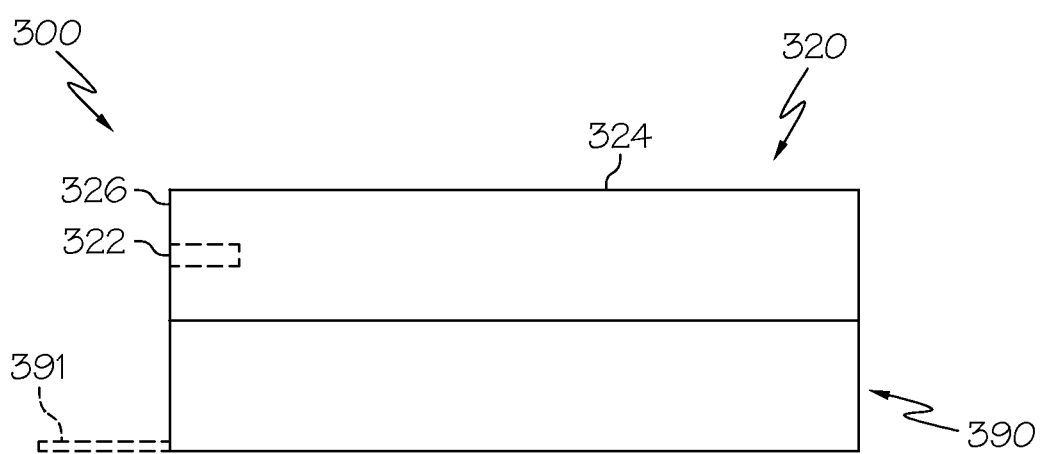
FIG. 3B is a side view of a limited-use blood glucose meter having a blood glucose test strip enclosure according to one or more embodiments described and illustrated herein.

Referring now to FIGS. 3A and 3B, another embodiment of a limited-use blood glucose meter 300 is illustrated. The limited-use blood glucose meter 300 is similar to the embodiment illustrated in FIGS. 1A-1C. However, the limited-use blood glucose meter 300 illustrated in FIGS. 3A and 3B further includes a blood glucose test strip enclosure 390 that is configured to maintain a plurality of blood glucose test strips. The blood glucose test strip enclosure 390 may be defined by the meter housing 320 and may be a single, integral component of the limited-use blood glucose meter 300. In another embodiment, the blood glucose test strip enclosure 390 may be a component that is separate from the meter housing 320 such that it may be removably coupled to the meter housing 320. The blood glucose test strip enclosure 390 may have an access door 391 that may be opened and closed to enable a user to access the strips within the enclosure. In another embodiment, a cap may be used to close the enclosure 390. Because humidity may affect the lifetime of the strips maintained within the blood glucose test strip enclosure 390, the limited-use blood glucose meter 300 may be programmed to operate for a duration of time that corresponds to a lifetime of a typical blood glucose test strip exposed to ambient air. For example, the lifetime of the limited-use blood glucose meter 300 may be limited to three days (or other durations) from the moment the access door 391 is opened. The access door 391 may have electrical contact pads that mate with the housing of the blood glucose test strip enclosure 390 such that a detection of loss of electrical contact between the access door 391 and the housing of the blood glucose test strip enclosure 390 causes a timer to begin counting down. When the timer expires, operational functions of the limited-use blood glucose meter 300 may be prevented. In another embodiment, each blood glucose test strip may be individually sealed in a wrapping to prevent ambient air from reaching the reagent of the strip.

Figure 4:
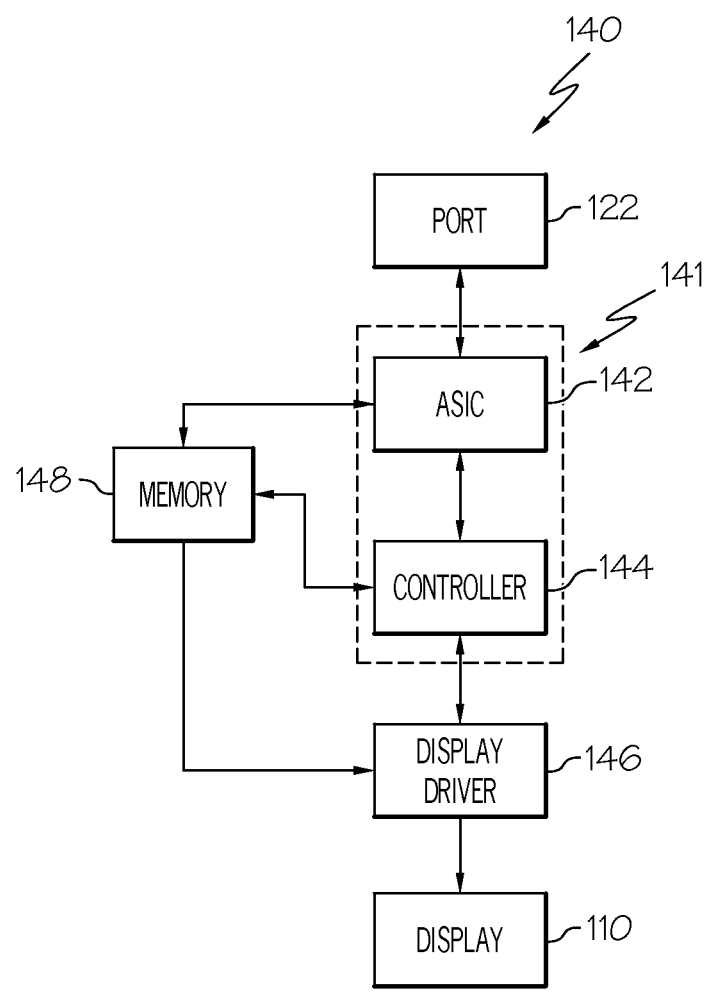
FIG. 4 is a schematic diagram of a printed circuit board assembly of a limited-use blood glucose meter according to one or more embodiments described and illustrated herein.

A printed circuit board assembly 140 will now be described with reference to FIGS. 4 and 5A-5C. FIG. 4 illustrates a schematic diagram of a printed circuit board assembly 140 disposed within the meter housing 120. FIG. 5A illustrates a first side of an exemplary printed circuit board assembly 140, FIG. 5B illustrates a second side of the exemplary printed circuit board assembly 140 illustrated in FIG. 5A, and FIG. 5C illustrates a cross section view of the exemplary printed circuit board assembly 140 illustrated in FIGS. 5A and 5B maintained within the meter housing 120 described above. In one embodiment, the printed circuit board assembly 140 includes a printed circuit board 143, a controller device 144, a strip reading device 142, a display controller 146, a bi-stable display 110, a memory device 148 and a strip port 122. Embodiments may also include a crystal 145 for clock function of the controller device 144 and/or strip reading device.

The printed circuit board components are mounted onto the printed circuit board 143 on either a first side 143a or a second side 143b. In another embodiment the printed circuit board assembly 140 may not include a separate memory device 148. Rather, the meter may make use of memory that is internal to the controller device 144 or the strip reading device 142.

The controller device 144 is programmed to perform meter operations such as instructing the strip reading device 142 to perform a blood glucose test, instructing the display controller 146 to update the bi-stable display 110, and performing timing functions among other operations. Program code may be stored in the controller device 144 to enable the controller device 144 to perform the functions and operations described herein. The controller device 144 is communicatively coupled to the strip reading device 142, the display controller 146 and the memory device 148. The printed circuit components described herein may be electrically connected by printed traces on or within the printed circuit board 143, by vias within the printed circuit board 143, and/or by wires or jumper connections, for example.

The controller device 144 may be a low-cost and low-power microcontroller. The low-cost and low-power microcontroller enables the cost of the limited-use blood glucose meter 100 to be relatively low, thereby making the limited-use blood glucose meter 100 disposable. As an example and not a limitation, the controller device 144 in one embodiment may be a MSP430FG4619 ultra low-power microcontroller manufactured by Texas Instruments Incorporated. Other ultra low-power microcontroller devices may be utilized to perform the functions of the controller device 144.

The strip reading device 142 is in electrical communication with the controller device 144 as well as the measurement strip port 112. The strip reading device 142 may be configured as an application specific integrated circuit ("ASIC"), and may be a mixed-signal device, having both digital and analog components. The strip port 122 is used to connect the blood glucose test strip 130 electrically to the strip reading device 142, which reads the test strip electronically as described in more detail below and provides an input to the controller device 144 for analysis. The strip reading device 142 is specifically configured to sample and read a blood glucose test strip provided to the strip port 122 upon receipt of an instruction signal from the controller device 144. In another embodiment, the strip reading device 142 may automatically detect the insertion of a blood glucose test strip into the strip port 122 and initiate a blood glucose measurement test without first receiving an instruction signal from the controller device 144.

More specifically, when a blood glucose test strip 130 is inserted into the strip port 122, the strip reading device 142 is operable to electrically detect the insertion and, subsequently, communicate with the strip port 122 such that the strip reading device 142 may receive signals from the blood glucose test strip 130 related to the blood glucose level of a blood sample placed on the reaction site. The strip reading device 142 may, after receiving the signals from the blood glucose test strip 130, process these signals and communicate information about the blood glucose level to the controller device 144. The controller device 144, in turn, may take this information and process it further in order to arrive at the final blood glucose measurement result. Thus, the strip reading device 142 and the controller device 144 may work together to perform the blood glucose measurement function, with the strip reading device 142 performing part of the function and the controller device 144 performing part of the function. The strip reading device 142 may be housed in an electrical ball-grid array (BGA) package or other suitable package. The strip reading device 142 may additionally perform other functions such as generating a fixed-frequency clock signal for the controller device 144. The strip reading device 142 and controller device 144 may communicate with each other via a serial bus, such as I$^2$C or serial peripheral interface ("SPI"), or via a parallel interface.

In another embodiment, the functions performed by the controller device 144 and the strip reading device 142 may be performed by a single integrated circuit device 141 rather than two separate components. The single integrated device 141 may be a mixed signal ASIC device capable of performing the functions described herein.

Still referring to FIGS. 4 and 5A-5C, the printed circuit board assembly 140 may also include a non-volatile (e.g., flash) memory device 148. This memory device may be external to the controller device 144, as is depicted in FIGS. 5A-5C, or may be integrated into the controller device 144 or the strip reading device 142. The memory device 148 may be operable to store information relating to the operation of the meter, such as configuration parameters, calibration data for the blood glucose test strips, and so forth. Further, the memory device may be operable to store a most-recent blood glucose level for access by the controller device 144 and the strip reading device 142. The memory device 148 may be in electrical communication with the strip reading device 142 such that the data stored in the memory device 148 may be read by the strip reading device 142. In addition, the strip reading device 142 may write data to the memory device 148 such that the data is stored on the memory device 148 in a non-volatile fashion. The memory device 148, when it is external to the microcontroller, may be a 68 kilobit device, for example. Other types of memory may also be utilized.

The display controller 146, which is electrically coupled to the bi-stable segments of the bi-stable display 110 via conductive traces running from outputs of the display controller 146 to the bi-stable segment electrodes, is configured to receive display instructions from the controller device 144 (e.g., display results of most recent blood glucose measurement test) as well as receive or otherwise obtain a most-recent blood glucose level. The display controller 146 applies appropriate charge pump voltages to the bi-stable segment electrodes via the display controller outputs. For example, the bi-stable segments may be switched from an "on" state to an "off" state by reversing the polarity of the voltage on the bi-stable segment electrodes.

More specifically, to individually control each bi-stable segment of the display, the display controller 146 may apply charge pump voltages to the top and bottom electrodes and reverse the voltage polarity to turn the bi-stable segments on and off. Conductive traces run from the outputs of the display controller 146 to the electrodes of the bi-stable segments within the bi-stable display 110. The display controller 146 may be used to integrate functions needed for driving the bi-stable display 110. Data may be clocked into the display controller 146 using a SPI before integrated charge pumps within the display controller 146 (or external charge pumps) generate the voltages required to drive the display. Once the display has been updated, the display controller 146 can be switched into standby or power-down mode while the image is retained on the display.

It is noted that other discrete components, such as resistors, capacitors, inductors, and diodes, that are not described herein may be needed to enable the operation and functionality of the embodiments described herein. These discrete components do not materially affect the basic and novel characteristics of the embodiments described and claimed herein. For example, capacitors and resistors may be utilized in the printed circuit board assembly 140 for noise filtering and/or microcontroller operational functions.

Referring now specifically to FIGS. 5A-5C, a printed circuit board assembly 140 and limited-use blood glucose meter 100 according to one embodiment is illustrated. It should be understood that the embodiments described herein are not limited by the configuration and component arrangement illustrated in FIGS. 5A-5C. FIG. 5A illustrates a first side 143*a* of a printed circuit board assembly 140. The first side 140*a* may be referred to as a top side because the bi-stable display is mounted on the first side. In the illustrated embodiment, the strip reading device 142, the crystal 145 and the bi-stable display 110 are all mounted on the first side 143*a*. The components described herein may be low-profile surface mount components that enable a small meter design.

FIG. 5B illustrates a second or bottom side 143*b* of the printed circuit board assembly 140. Mounted on the second side 143*b* are the strip port 122, the controller device 144, the display controller 146, the memory device 148, and a power source 147. Because the limited-use blood glucose meter 100 is disposable, the power source 147 may be a non-replaceable battery. Further, as described in more detail below, the battery may have a limited charge such that it expires after a relatively short time, thereby limiting the life of the limited-use blood glucose meter 100. The power source may be maintained on the printed circuit board 143 and within the meter housing 120 such that it is inaccessible to the user. Inaccessible means that the power source 147 cannot be removed from the limited-use blood glucose meter 100 without causing damage to the meter housing 120 and/or the printed circuit board 143.

As illustrated in FIGS. 5A-5C, the strip reading device 142 should be mounted on the printed circuit board 143 as close as possible to the strip port 122 to achieve the most accurate blood glucose measurement possible. Positioning the strip reading device 142 far from the strip port 122 may introduce inaccuracies in the blood glucose measurement. In the illustrated embodiment, the strip reading device 142 is mounted on the printed circuit board 143 directly opposite from the strip port 122. The strip reading device 142 may be electrically coupled to the strip port 122 by one or more vias that run through the printed circuit board 143. The strip port 122 may have electrical contacts (not shown) that make electrical contact with the electrodes 132, 134 of the blood glucose test strip 130.

Figure 6:
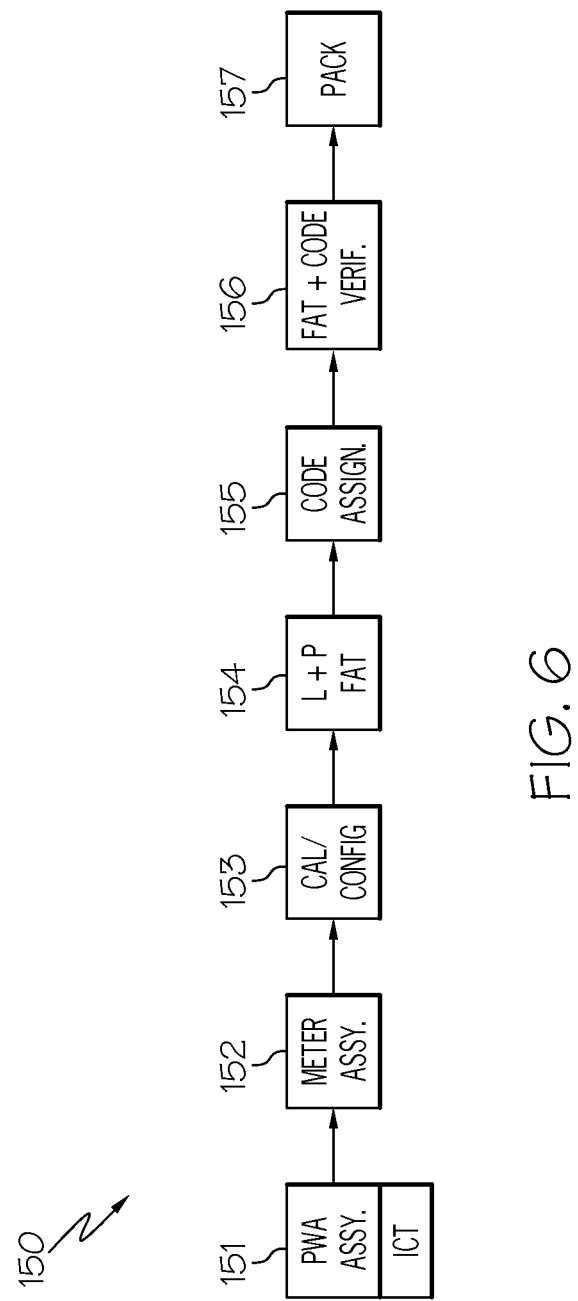
FIG. 6 is a flow chart diagram of a fabrication process of a limited-use blood glucose meter according to one or more embodiments described and illustrated herein.

As depicted in FIG. 6, the printed circuit board assembly 140 may be disposed within an enclosure defined by the meter housing 120. Because of the arrangement and small size of the components, the limited-use blood glucose meter 100 is relatively thin. The bi-stable display is mounted on the first side 143*a* of the printed circuit board 143 and is positioned such that it is aligned with the lens 127 of the meter housing 120. In this manner, the bi-stable display 110 may be visible to a user. The lens 127 may be made of a transparent material, such as plastic or glass, for example. The meter housing 120 may be made of a rigid material such as a plastic material, for example. The strip port opening 123 of the meter housing 120 may have a chamfer to aid the user in inserting a blood glucose test strip into the strip port 122.

Referring now to FIG. 6, a manufacturing and assembly process of one embodiment of the limited-use blood glucose meter is illustrated in a flow chart 150. At block 151, the printed circuit board is populated with the components described above to assemble the printed circuit board assembly. The components, which may be surface mount components, may be robotically or manually mounted to the printed circuit board. After assembly, the printed circuit board assembly may be subjected to an in-circuit test wherein each electrical node of the circuit is tested for proper functionality. If the printed circuit board assembly passes the in-circuit test, it is the positioned and sealed within the meter housing at block 152. This process may be robotic or manual.

After the limited-use blood glucose meter is assembled, it may be calibrated and/or configured at block 153. The meter may be calibrated to instruct the strip reading device as to what type of blood glucose testing strip are intended to be utilized with the limited-use blood glucose meter. Various types of strips may use different chemistry as the reagent to perform the blood glucose measurement test. During the calibration step, the type of blood glucose testing strip may be written and stored into the memory device. During the configuration step, the desired units (mg/dL or mmol/L) that are to be displayed is written to the memory device.

As an example and not a limitation, the meter housing may comprise a plurality of programming openings that expose a plurality of programming contact pads. To write to the memory device to calibrate and configure the meter, a programming connector may be placed on the meter housing at the programming openings to read and write information to the memory device. After calibration, programming and code assignment (described below), a label may be placed over the programming openings. In another embodiment, the meter may be programmed by inserting a programming device into the strip port.

After the calibration and configuration step at block 153, the limited-use blood glucose meter may then be subjected to a light-and-play test and a final acceptance test. The light-and-play test ensures that the bi-stable display works properly. In one embodiment, all of the segments turn on and off to verify correct operation. In another embodiment, each segment is turned on individually in a pattern. The segments may be sequenced in any number of patterns. During the final acceptance test, a blood glucose test strip simulator is inserted into the strip port and test signals are generated to simulate a blood glucose measurement.

If the limited-use blood glucose meter passes the light-and-play and final acceptance tests, a code value corresponding to a chemical lot code of the blood glucose test strips that are to be packaged with the limited-use blood glucose meter is written to the memory device at block 155. The code may be written utilizing the programming openings or the strip port as described above. Use of the code increases the accuracy of the limited-use blood glucose meter. At block 156, a second final acceptance test may be performed using the written code. During this step, the correct code is verified. If the code is correct and the simulated blood glucose measurement of the final acceptance test is within an acceptable range, a label having a serial number and other information may be place on the meter housing (e.g., over the programming openings, if present). The limited-use blood glucose meter may be packaged with a number of blood glucose test strips for sale to consumers.

Operation of one embodiment of a limited-use blood glucose meter will now be described. A user in need of an inexpensive and quick blood glucose measurement for any reason may purchase a limited-use blood glucose meter from a retailer or be given a meter from a doctor or other caregiver. The user may be a diabetic who does not have current access to his or her everyday blood glucose meter (or is going to be undertaking activities that may be hazardous to a blood glucose meter such as canoeing or camping), a person who may be pre-diabetic and desires to determine whether or not he or she is diabetic, a pregnant woman who may be diagnosed with gestational diabetes, etc.

The limited-use blood glucose meter is packaged with a certain number of blood glucose test strips and is programmed to only perform a number of blood glucose measurements that equals the number of blood glucose test strips that are originally contained in the package. Also included is a lancet that the user may use to draw a blood sample. In one embodiment, a form may be included in the package. The user may use the form to record the blood glucose measurements. The form may include a graph portion that the user may use to plot the test data to determine whether or not he or she is diabetic, or if his or her insulin treatment is effective. The user may take the data recorded on the form and enter it into a computer program that tracks basal and pre- and post-prandial blood glucose measurements.

The user removes a blood glucose measurement test strip from the package. In one embodiment, the blood glucose measurement test strip may be stored in a blood glucose test strip enclosure as described above. Or, in another embodiment, the blood glucose test strip may be stored in a separate vial. The user positions the blood glucose test strip onto the strip port. Electrodes on the blood glucose test strip are detected by the controller device and the limited-use blood glucose meter is awakened from a power-down state. The user then pricks his or her finger with the provided lancet to create a drop of blood and places the drop of blood onto the blood glucose test strip at the appropriate test location. The drop of blood reacts with the reagent chemistry of the test strip and electrical blood glucose signals are generated corresponding with the blood glucose level of the drop of blood. The strip reading device probes the sample drop of blood and determines the blood glucose level, as well as if the test was valid. In one embodiment, the strip reading device writes the determined blood glucose level to the memory device. In another embodiment, the strip reading device sends the blood glucose level to the controller device, which may then write the blood glucose level to the memory device.

If the blood glucose level is written to the memory device, the controller device instructs the display controller to read the blood glucose level from the memory device and to apply charge pump voltages to the segments of the bi-stable display such that the bi-stable display displays the blood glucose level (i.e., the most-recent blood glucose level) as well as the proper units and good/bad symbol. In another embodiment, the controller device may send the blood glucose level directly to the display controller. After a predetermined amount of time following the update to the bi-stable display, the limited-use blood glucose meter goes into power-down mode. However, the bi-stable display persistently displays the most-recent blood glucose level despite that the meter is in an off state. The process described above is repeated for a subsequent blood glucose measurement test.

Once all of the blood glucose test strips have been used, the predetermined number of blood glucose measurements have been performed, or the life of the limited-use blood glucose meter has expired (i.e., a timer has expired or the charge of the power supply is depleted), the meter ceases all functions. The bi-stable display may display a message indicating that the life of the meter has expired (or may continue to display the most-recent blood glucose level). The user may then dispose of the limited-use blood glucose meter.

Embodiments described herein are low-cost limited-use blood glucose meters that users may utilize for a predetermined period of time or number of tests and then dispose of. Use of a persistent bi-stable display provides that embodiments do not need to incorporate expensive memory devices to store test results, or communications modules to communicate results to a computer or other device. Embodiments provide a low-cost alternative to expensive blood glucose measurement devices for those who are not in need of such expensive devices, such as pre-diabetics, those with gestational diabetes, traveling diabetics, and many others. Embodiments enable meter manufactures to provide a low-cost meter in packaging along with blood glucose test strips.

It is noted that recitations herein of a component of embodiments of the present specification being "configured," "programmed" or "operable" in a particular way, "configured," "programmed" or "operable" to embody a particular property, or function in a particular manner, are structural recitations as opposed to recitations of intended use. More specifically, the references herein to the manner in which a component is "configured," "programmed" or "operable" denotes an existing physical condition of the component and, as such, is to be taken as a definite recitation of the structural characteristics of the component.

It is noted that one or more of the following claims utilize the term "wherein" as a transitional phrase. For the purposes of defining the embodiments of the present specification, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A low-cost, limited-use blood glucose meter that is programmed or otherwise configured to only perform a predetermined number of blood glucose measurement tests that equals the number of blood glucose test strips associated with the limited-use blood glucose meter and originally contained in a package, comprising:

a meter housing;

a printed circuit board assembly, the printed circuit board assembly comprising:

a power source comprising a non-removable battery mounted on a side of the printed circuit board assembly that is sealed within the meter housing and which is inaccessible to the user and cannot be removed from the limited-use blood glucose meter without causing damage to the meter housing or the printed circuit board;

a strip port which accepts a blood glucose test strip having a blood glucose reagent;

a strip reading device electrically coupled to the strip port which measures a reaction between a blood sample present on the blood glucose test strip and the blood glucose reagent, generates a blood glucose signal corresponding with the measured reaction, and which calculates a blood glucose level based at least in part on the blood glucose signal;

a controller device communicatively coupled to the strip reading device, wherein the controller device receives the blood glucose level from the strip reading device;

a bi-stable display comprising a plurality of bi-stable segments which transition between an on-state and an off-state with the application of drive voltages, wherein the bi-stable segments are arranged to display the blood glucose level, and wherein the bi-stable display persistently displays a most-recent blood glucose level without power provided by the power source; and a display controller communicatively coupled to the controller device and the bi-stable display, wherein the controller device provides display instructions to the display controller and the display controller provides drive voltages to the bi-stable segments based on the blood glucose level such that the bi-stable segments persistently display the most-recent blood glucose level; and wherein the strip reading device performs the predetermined number of blood glucose measurement tests and calculates the blood glucose level, and once the predetermined number of blood glucose measurement tests have been performed, the controller device of the limited-use blood glucose meter is programmed to cease all functions.

2. The limited-use blood glucose meter according to claim 1, further comprising the meter housing defining an enclosure in which the printed circuit board assembly is disposed such that the bi-stable display is aligned with the lens, the lens being dimensioned such that the bi-stable display is visible through the lens; and the strip port opening is aligned with the strip port and sized to accept the blood glucose test strip.

3. The limited-use blood glucose meter according to claim 2, wherein the meter housing further comprises a blood glucose test strip enclosure to store the blood glucose test strips associated with the limited-use blood glucose meter.

4. The limited-use blood glucose meter according to claim 3, wherein:
the controller device detects when the blood glucose test strip enclosure is opened for a first time and initiates a timer; and
expiration of the timer causes all the functions of the limited-use blood glucose meter to cease such that operational functions of the limited-use blood glucose meter is prevented.

5. The limited-use blood glucose meter according to claim 1, wherein the bi-stable display persistently displays the most-recent blood glucose level until a subsequent blood glucose level is calculated.

6. The limited-use blood glucose meter according to claim 1, wherein the bi-stable display comprises an e-paper display.

7. The limited-use blood glucose meter according to claim 1, wherein:
the bi-stable display comprises a good blood glucose symbol and a bad blood glucose symbol;
the good blood glucose symbol is activated when the most-recent blood glucose level is within a good blood glucose level range; and
the bad blood glucose symbol is activated when the most-recent blood glucose level is not within the good blood glucose level range.

8. The limited-use blood glucose meter according to claim 1, further comprises a timer, wherein expiration of the timer causes all the functions of the limited-use blood glucose meter to cease such that operational functions of the limited-use blood glucose meter is prevented.

9. The limited-use blood glucose meter according to claim 1, further comprising a memory device, wherein the memory device stores a code value that corresponds to a lot code of the blood glucose test strips.

10. The limited-use blood glucose meter according to claim 1, wherein the number of blood glucose measurement tests is limited by software.

11. The limited-use blood glucose meter according to claim 1, wherein the limited-use blood glucose meter is programmed to operate with a selected one of a plurality of test strip types.

12. The limited-use blood glucose meter according to claim 1, wherein the limited-use blood glucose meter is powered on when the blood glucose test strip is inserted into the strip port and is automatically powered down after a predetermined time following the display controller providing drive voltages to the bi-stable display.

13. The limited-use blood glucose meter according to claim 1, further comprising a memory device communicatively coupled to the strip reading device and the controller device, wherein:
the strip reading device writes the most-recent blood glucose level to the memory device; and
the controller device instructs the display controller to read the memory device to obtain the most-recent blood glucose level and provide the drive voltages to the bi-stable display.

14. A low-cost, limited-use blood glucose meter that is programmed or otherwise configured to only perform for a user a predetermined number of blood glucose measurement tests that equals the number of blood glucose test strips associated with the limited-use blood glucose meter and originally contained in a package, comprising a housing and a printed circuit board assembly, the printed circuit board assembly provided in the housing comprising:
a non-removable battery mounted on a side of the printed circuit board assembly that is sealed within the housing and which is inaccessible to the user and cannot be removed from the limited-use blood glucose meter without causing damage to the housing or the printed circuit board;
a strip port which accepts a blood glucose test strip having a blood glucose reagent;
a strip reading device electrically coupled to the strip port which measures a reaction between a blood sample present on the blood glucose test strip and the blood glucose reagent, generates a blood glucose signal corresponding with the measured reaction, and which calculates a blood glucose level based at least in part on the blood glucose signal;
a controller device communicatively coupled to the strip reading device, wherein the controller device receives the blood glucose level from the strip reading device;
a bi-stable display comprising a plurality of bi-stable segments which transition between an on-state and an off-state with the application of drive voltages, wherein the bi-stable segments are arranged to display the blood glucose level, and wherein the bi-stable display persistently displays a most-recent blood glucose level without power provided by the non-removable battery until a subsequent blood glucose level is calculated; and
a display controller communicatively coupled to the bi-stable display, wherein the display controller receives display instructions regarding the blood glucose level from the controller device and provides drive voltages to the bi-stable segments based on the blood glucose level such that the bi-stable segments persistently display the most-recent blood glucose level; and
wherein the strip reading device performs the predetermined number of blood glucose measurement tests and calculates the blood glucose level, and once the predetermined number of blood glucose measurement tests have been performed, the controller device of the limited-use blood glucose meter is programmed to cease all functions.

15. The limited-use blood glucose meter according to claim 14, the housing comprising a blood glucose test strip enclosure to store blood glucose test strips associated with the limited-use blood glucose meter.

16. The limited-use blood glucose meter according to claim 15, wherein:
the controller device detects when the enclosure is opened for a first time and initiates a timer; and expiration of the timer causes all the functions of the limited-use blood glucose meter to cease such that operational functions of the limited-use blood glucose meter is prevented.

17. A low-cost, limited-use blood glucose meter that is programmed or otherwise configured to only perform for a user a predetermined number of blood glucose measurement tests that equals the number of blood glucose test strips associated with the limited-use blood glucose meter and originally contained in a package, comprising:

a meter housing; and a printed circuit board assembly provided in the meter housing and consisting essentially of:

a non-removable battery mounted on a side of the printed circuit board assembly that is sealed within the meter housing and which is inaccessible to the user and cannot be removed from the limited-use blood glucose meter without causing damage to the meter housing or the printed circuit board;

a strip port which accepts a blood glucose test strip having a blood glucose reagent;

a strip reading device electrically coupled to the strip port which measures a reaction between a blood sample present on the blood glucose test strip and the blood glucose reagent, generates a blood glucose signal corresponding with the measured reaction, and which calculates a blood glucose level based at least in part on the blood glucose signal;

a controller device communicatively coupled to the strip reading device, wherein the controller device receives the blood glucose level from the strip reading device;

a bi-stable display comprising a plurality of bi-stable segments which transition between an on-state and an off-state with the application of drive voltages, wherein the bi-stable segments are arranged to display the blood glucose level, and wherein the bi-stable display persistently displays a most-recent blood glucose level without power provided by the non-removable battery;

a display controller communicatively coupled to the controller device and the bi-stable display which provides drive voltages to the bi-stable segments based on the blood glucose level such that the bi-stable segments persistently display the most-recent blood glucose level; and a memory device communicatively coupled to the strip reading device and the controller device, wherein the memory device stores the most-recent blood glucose level, and the display controller retrieves the most-recent blood glucose level from the memory device upon instruction from the controller device, and wherein the meter housing comprising a lens and a strip port opening, wherein:

the meter housing defines an enclosure in which the printed circuit board assembly is disposed such that the bi-stable display is aligned with the lens, the lens being dimensioned such that the bi-stable display is visible through the lens; and the strip port opening is aligned with the strip port and sized to accept the blood glucose test strip, and wherein the strip reading device performs the predetermined number of blood glucose measurement tests and once the predetermined number of blood glucose measurement tests have been performed, the controller device of the limited-use blood glucose meter is programmed to cease all functions.

18. The limited-use blood glucose meter according to claim 17, wherein the non-removable battery ceases to operate after a predetermined time that corresponds with an expiration date of the limited-use blood glucose meter.

19. The limited-use blood glucose meter according to claim 8, wherein the expiration of a duration of time that corresponds to a lifetime of a blood glucose strip exposed to ambient air causes all the functions of the limited-use blood glucose meter to cease.

* * * * *